United States Patent
Gomis De Barbara et al.

(10) Patent No.: US 7,122,209 B2
(45) Date of Patent: Oct. 17, 2006

(54) ORAL COMPOSITIONS FOR THE TREATMENT OF NON-DIABETIC OBESE MAMMALS, INCLUDING HUMANS

(75) Inventors: Ramon Gomis De Barbara, Barcelona (ES); Marc Claret Carles, Barcelona (ES); Joan-Josep Guinovart Cirera, Barcelona (ES); Josefa Fernandez Alvarez, Barcelona (ES)

(73) Assignee: Quimica Farmaceutica Bayer S.A., (ES)

( * ) Notice: Subject to any disclaimer, the term of this patent is extended or adjusted under 35 U.S.C. 154(b) by 250 days.

(21) Appl. No.: 10/477,807

(22) PCT Filed: May 16, 2002

(86) PCT No.: PCT/ES02/00231

§ 371 (c)(1),
(2), (4) Date: Nov. 14, 2003

(87) PCT Pub. No.: WO02/098435

PCT Pub. Date: Dec. 12, 2002

(65) Prior Publication Data

US 2004/0131697 A1    Jul. 8, 2004

(30) Foreign Application Priority Data

May 16, 2001    (ES) ................ 200101200

(51) Int. Cl.
*A61K 33/24*    (2006.01)
*A61P 3/04*    (2006.01)

(52) U.S. Cl. .............. 424/617; 514/492; 514/909
(58) Field of Classification Search ........... 424/617; 514/909
See application file for complete search history.

(56) References Cited

U.S. PATENT DOCUMENTS 5,595,763 A * 1/1997 Guinovart et al. .......... 424/617

FOREIGN PATENT DOCUMENTS

ES    2 108 642    12/1997
JP    60 02 5 928    2/1985

OTHER PUBLICATIONS

Cecil Textbook of Medicine, W.B. Saunders Co., Philadelphia, 1992, vol. 2, p. 1166.*
J. Matsumoto, "Vanadate, Molybdate and Tungstate for Orthomolecular Medicine". Medical Hypotheses, 1994, vol. 43, p. 177-182, p. 179, table 1.
J.D. Foster et al, "Tungstate: a Potent Inhibotor of multifunctional Glucose-6-Phasphatase". Archiv. Biochem. Biophys., 1998, vol. 354, No. 1, p. 125-132.
International Search Report, 2002.

* cited by examiner

*Primary Examiner*—John Pak
(74) *Attorney, Agent, or Firm*—Ostrolenk, Faber, Gerb & Soffen, LLP

(57) ABSTRACT

Oral compositions containing an effective amount of a tungsten compound (VI), preferably a tungstate salt, more preferably sodium tungstate ($Na_2WO_4$), are useful in controlling obesity/overweightness in non-diabetic mammals, including humans. The anti-obesity effect of sodium tungstate dihydrate in rats has been determined in a cafeteria-diet-induced obesity model. Said obese rats are good models of obese, non-diabetic mammals, including humans. The prophylactic, therapeutic and/or cosmetic treatment resulting from this invention is surprising. It provides advantages such as effectiveness, lack of toxicity and relatively low price in comparison with other treatments in prior art. Hence, the oral compositions according to the invention are useful for the treatment of obesity/overweightness in non-diabetic mammals, including humans.

5 Claims, 2 Drawing Sheets

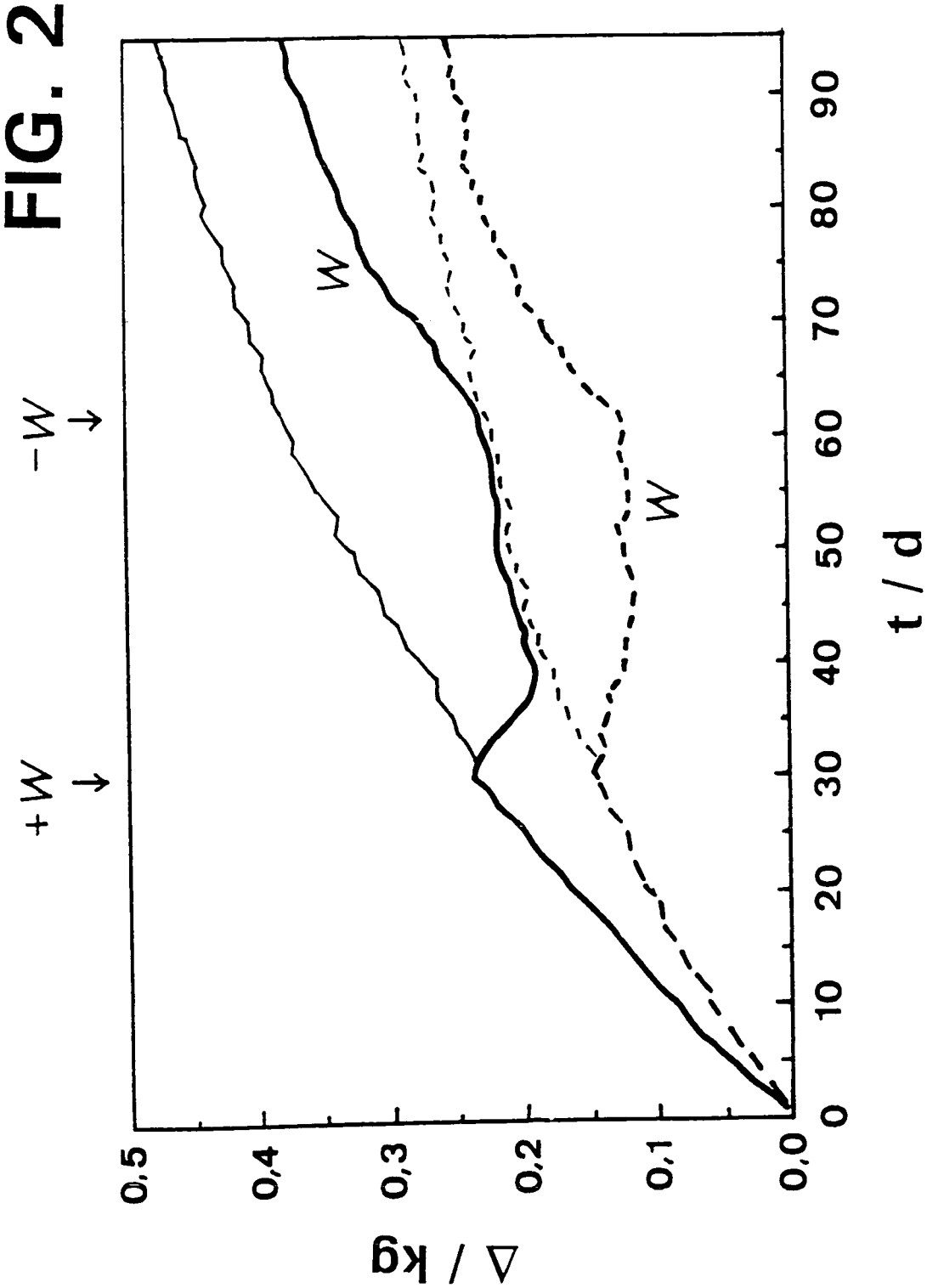

ORAL COMPOSITIONS FOR THE TREATMENT OF NON-DIABETIC OBESE MAMMALS, INCLUDING HUMANS

This application is a 371 of PCT/ES02/00231, filed on May 16, 2002, which claims benefit of priority to ES 200101200, filed on May 16, 2001.

The invention refers to the use of oral compositions for the treatment of non-diabetic mammals, including humans suffering from obesity and/or overweight. The active principles of these compositions are compounds which have never been suggested for that use, although some of them are chemically-known.

BACKGROUND ART

Obesity/overweight is a chronic metabolic disorder in which excess of body fat causes or increases the risk of suffering many health problems. In particular, it is associated with coronary heart disease, development of certain forms of cancer, respiratory problems, and cholelithiasis. It is a complex disorder determined by interactions between genetic, environmental and psychosocial factors that affect the balance between energy intake and expenditure. Human obesity, defined as a body-mass index higher than 30 Kg/m$^2$, is a major and costly disease in developed countries, with an approximate prevalence of 15–20% in Europe and 20–25% in United States. However it is also present, and increasing, in Latin America and Southeast and Middleast Asia. Despite the importance of obesity as a medical and social problem, nowadays there is not any totally effective treatment available.

Attempts to solve the problem of obesity/overweight by reducing food intake, with o without antiorexic therapy, or by doing physical exercise, are well known. But also known are the difficulties, limitations and general lack of success of all these approaches. Pharmacotherapy of obesity/overweight has been studied by using e.g. dexfenfluramine, sibutramine, orlistat and phentermine; but none of these agents has proved to be totally satisfactory.

U.S. Pat. No. 5,595,763 teaches the use of tungsten (VI) compositions as insulin-mimicker drugs for the treatment of human suffering from diabetes mellitus. Although humans suffering from type 2 diabetes (non-insulin-dependent diabetes mellitus; NIDDM) may also show obesity symptoms, both pathologies (diabetes and obesity) are considered clinically different from each other. Actually, many humans suffering from obesity are never considered as diabetic. The present invention specifically refers to the treatment of obesity in the patient population of non-diabetic, obese humans. Tungsten compounds have never been suggested for such a treatment.

Thus, the provision of new products for the treatment of obesity/overweight in non-diabetic mammals, including humans, is still of major importance.

DISCLOSURE OF THE INVENTION

According to an aspect of the present invention, there is provided an oral composition for the prophylactic, therapeutic and/or cosmetic treatment of obesity/overweight in non-diabetic mammals, including humans, said composition comprising an effective amount of a compound formed by tungsten (VI) and a pharmaceutically acceptable chemical moiety, or of a solvate of said compound, in combination with pharmaceutically acceptable excipients.

In the context of this invention, the expression "a compound formed by tungsten (VI) and a pharmaceutically acceptable chemical moiety" is intended to include any chemical entity formed by one or several tungsten atoms in its 6+ oxidation state attached to a chemical structure that is pharmaceutically acceptable by itself. The cation $W^{6+}$ has neither been observed nor isolated, and it comes always accompanied with a chemical moiety partially formed by a coordination sphere around the atom of W(VI). The coordination sphere can be formed by inorganic ligands (oxide, hydroxide, peroxide, etc.) as, for example, in the case of the tungstate anion (coordination sphere formed by four oxide ions), or in the case of peroxytungstates (coordination sphere formed by mixtures of oxide and peroxide ions). The coordination sphere can also be formed by organic ligands which are molecules or ions attached to W(VI) atom through O, S or N atoms belonging to different pharmaceutically acceptable organic compounds (e.g. pharmaceutically acceptable alcohols, thiols, carboxylic acids, amines, aminoacids, N-containing heterocycles, etc.). Mixed inorganic/organic coordination spheres are also possible. When the structure formed by the W(VI) atom and its coordination sphere is not neutral, the term "chemical moiety" also includes any pharmaceutically acceptable ionic species which makes neutral the whole tungsten (VI) compound. For example, the tungstate anion is always accompanied by a cation (e.g. sodium, potassium, magnesium, calcium) to form a neutral tungstate salt. Tungstate ion gives rise to a series of isopolytungstates (paratungstates, metatungstates, etc.) which differ in the degree of aggregation; their use is also contemplated in this invention. Solvates of tungsten (VI) compounds are common (e.g. the dihydrate of sodium tungstate), and their use is also considered part of this invention.

Another aspect of the present invention relates to the use of a compound formed by tungsten (VI) and a pharmaceutically acceptable chemical moiety, or of a solvate of said compound, for the preparation of an oral composition for the prophylactic, therapeutical and/or cosmetic treatment of obesity/overweight in non-diabetic mammals, including humans.

The invention also relates to a method of prophylactic, therapeutical and/or cosmetic treatment of a non-diabetic human suffering from obesity/overweight, said method comprising the oral administration of an effective amount of a compound formed by tungsten (VI) and a pharmaceutically acceptable chemical moiety, or of a solvate of said compound, in combination with pharmaceutically acceptable excipients.

In a preferred embodiment, the tungsten (VI) compound in the pharmaceutical composition of this invention is a salt of tungstate. Specially preferred are the salts of cationic moieties selected from the group consisting of sodium, potassium, magnesium and calcium cations. The most preferred tungsten (VI) compounds are sodium tungstate ($Na_2WO_4$) and its dihydrate. The latter is commercially available.

Sodium tungstate dihydrate is a white, odorless salt with fine and crystalline texture, and it is easily dissolved in water. The product can be administered via any conventional oral delivery system, the tablet format being the preferred one. The preferred daily dose of sodium tungstate dihydrate is between 0.5 and 50 mg/kg.

In the accompanying examples, the anti-obesity effect of sodium tungstate dihydrate in an rat model of diet-induced obesity called "cafeteria diet" has been assessed. These obese rats are a good model of non-diabetic obese mammals, including humans. The therapeutic and/or cosmetic effect on obesity/overweight associated to this invention is surprising and represents some advantages over other treatments proposed in the art. Among these advantages, efficiency is surely an evident one. Nevertheless, safety (lack of toxicity of tungsten compounds) and relatively low price (use of known affordable commercial products) are important as well. The weight loss is obtained without decrease of food intake.

BRIEF DESCRIPTION OF THE DRAWINGS

FIG. 2 depicts the evolution of body weight increase ($\Delta$ in kilograms) with time (t in days) along the three periods of the experiment, namely: induction of obesity (between day 0 and +W), tungstate treatment (from +W to −W), and recovery (from −W to the end).

DETAILED DISCLOSURE OF SPECIFIC EMBODIMENTS

Figure 1:
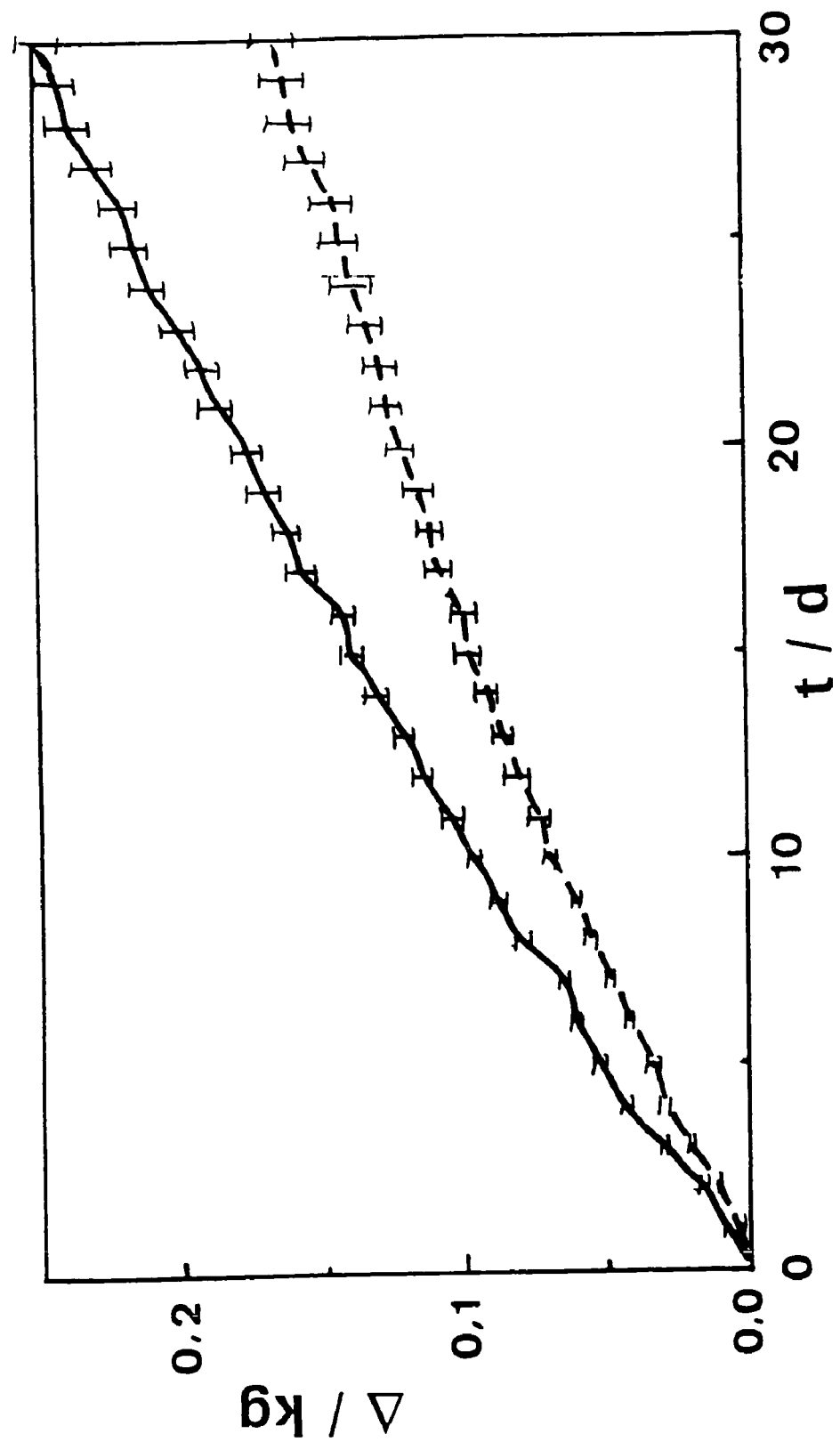
FIG. 1 depicts the evolution of body weight increase ($\Delta$ in kilograms) with time (t in days) along the first 30 days of the study, both for the standard-fed rats (dash line) and the cafeteria-fed ones (solid line).

The following examples illustrate the invention, but should be considered non-limitative.

EXAMPLE 1

Feeding of Rats Used in the Experiments: Standard Versus Cafeteria Diet

The so-called "cafeteria diet" consists of an offering of freshly and highly palatable supermarket food items with high fat and/or carbohydrate content in addition to standard laboratory chow. It is known that cafeteria-fed rats increase significantly the energy intake (as much as 60%) and body weight gain (50–200%) when compared to animals fed with only standard chow. Moreover, it is also known that ingestion of a cafeteria diet results in increased thermogenesis and fat deposition.

For the present experiments, male Wistar rats (IFFA CREDO), weighing 0.20–0.22 kg, were caged individually in a 12:12-h light-dark cycle, temperature and humidity controlled environment. After an adaptation period of 1 week the animals were divided into two dietary groups. One group was fed standard chow diet (2.7% in fat content, type AO4 from Panlab, Barcelona, Spain) and the second group was fed a cafeteria diet (30% in fat content). The cafeteria diet consisted of a daily offering of cookies, liver pate, bacon, standard chow and whole milk supplemented with 333 g/l sucrose and 10 g/l of a mineral and vitamin complex (Gevral, Cynamid Ibérica, Madrid, Spain). All the food items were weighed and presented in excess.

EXAMPLE 2

Experimental Design

An initial set of forty rats were divided into two sets of dietary conditions, control (standard diet, n=15) and cafeteria (cafeteria diet, n=25), and fed for 30 days. In order to evaluate the effects of tungstate treatment, animals from each condition were divided into two new subsets: tungstate treated and tungstate untreated groups (simply treated and untreated in the following). The treated rats were given a solution of 2 mg/ml of sodium tungstate dihydrate in distilled water.

The treatment was carried out for 32 days. Blood glucose measurements as well as blood samples were collected before (days 0–30), during (days 31–62) and at the end of the experimental period. Selective food items consumption (corrected by the amount of water lost for each) and the weight of all animals were recorded daily.

At the end of the treatment period, rats from treated (n=8) and untreated (n=7) cafeteria-fed groups and rats from both treated (n=3) and untreated (n=3) standard-fed groups were killed and several tissues (gastrocnemius muscle, intercapular brown adipose tissue (iBAT), epididimal white adipose tissue (WAT), liver, pancreas and brain) were excised, weighed, cleaned and rapidly frozen in liquid nitrogen or fixed in formol 10% for future studies.

Remaining rats (n=19) were withdrawn the tungstate treatment, but maintained the dietary conditions, in order to start a 35 day recovery period. After this time animals were killed and processed as above. Selective food items consumption (corrected by the amount of water lost for each) and the weight of all animals were recorded daily.

A complete summary of the experimental set-up is shown below, by describing the different groups of rats studied, starting with a total initial set of 40 male Wistar rats (n=40):

(1) Fed with cafeteria diet for 30 days (n=25; solid lines in the figures).
 (1.1) Fed with cafeteria diet and tungstate (W), for further 32 days (n=12; thick solid line).
  (1.1.1) Killed and analyzed (n=8).
  (1.1.2) Fed with cafeteria diet only for further 35 days, to check recovery (n=4).
 (1.2) Fed with cafeteria diet only, for further 32 days (n=13; thin solid line).
  (1.2.1) Killed and analyzed (n=7).
  (1.2.2) Fed with cafeteria diet only for further 35 days, to check recovery (n=6).
(2) Fed with standard diet for 30 days (n=15; dash lines in the figures).
 (2.1) Fed with standard diet and tungstate (W), for further 32 days (n=7; thick dash line).
  (2.1.1) Killed and analyzed (n=3).
  (2.1.2) Fed with standard diet only for further 35 days, to check recovery (n=4).
 (2.2) Fed with standard diet only, for further 32 days (n=8; thin dash line).
  (2.2.1) Killed and analyzed (n=3).
  (2.2.2) Fed with standard diet only for further 35 days, to check recovery (n=5).

EXAMPLE 3

Induction of Obesity Period (0–30 Days)

The first step of this study was to develop diet-induced obesity in cafeteria fed-rats. After a 30-day period of cafeteria feeding, the majority of rats showed a significant increase in body weight compared to standard-fed rats. FIG. 1 depicts the evolution of body weight increase ($\Delta$ in kilograms) with time (t in days) along the first 30 days of the experiment, both for standard-fed rats (dash line) and for cafeteria-fed rats (solid line). The mean percentage value of body weight increase at day 30 was 73% in standard-fed rats (dash line) and 106% in cafeteria fed-rats (solid line). Values are expressed as mean±SEM (standard error of the mean), for n=15 and n=25, respectively.

The data obtained in this study allowed to establish an obesity criteria. A rat was classified as obese when presenting an increase in body weight higher than 88% at the end of cafeteria feeding respect to the initial weight. Using this criteria the efficiency of the model of diet-induced obesity was higher than 90%.

EXAMPLE 4

Tungstate Treatment Period (31–62 Days)

FIG. 2 depicts the evolution of body weight increase (Δ in kilograms) with time (t in days) along the three periods of the experiment, namely: the obesity induction period (from day 0 to day 30, the later marked with +W), the tungstate treatment period (from day 31 to day 62, the latter marked with −W), and the recovery period (from day 63 to day 97).

The part of FIG. 2 between marks +W and −W indicate that tungstate administration significantly diminished body weight increase in both standard-fed rats (dash lines) and cafeteria-fed rats (solid lines). This is clearly apparent from the respective distances between the two thick lines (marked with W; solid=cafeteria; dash=standard) and their corresponding thin lines (references, without W). Standard-fed rats showed a marked reduction of body weight increase in relation to untreated rats from the first day of tungstate administration. However, this body weight reduction pattern disappeared at day 45 and became stable until the end of the treatment period. Tungstate slimming-effect in cafeteria treated rats was similar to that observed in standard treated rats, with an initial diminution of body weight increase and a trend to weight stability from day 40. The body weight increase evolution of both untreated-cafeteria and untreated-standard rats was unaltered (thin lines).

EXAMPLE 5

Recovery Period (63–97 Days)

The purpose of the recovery period was to investigate the reversibility of tungstate treatment. Thus, when tungstate treatment was withdrawn (point marked as −W in FIG. 2), both cafeteria and standard rats started to gain body weight quickly. Standard treated rats (thick solid line) increased their body weight as far as standard untreated rats (thick dash line). On the other hand, cafeteria treated rats showed an unquestionable body weight increase trend. However, at day 97 the body weight increase difference between cafeteria treated and untreated rats was quite important. This difference was probably due to the fact that weight increase difference generated at day 62 between treated/untreated cafeteria rats was larger than the corresponding one between treated/untreated standard rats. This difference means that, a long time after the end of the treatment, the tungstate treatment had caused a greater permanent slimming effect on rats suffering from obesity/overweight than on standard rats.

EXAMPLE 6

Preparation of Pharmaceutical Compositions for Oral Use

Two types of tablets, A and B, both containing 200 mg of sodium tungstate dihydrate per tablet, were prepared by standard compression techniques with the following two sets of excipients, respectively:

|  | Weight (mg/tablet) |
|---|---|
| Excipients A | |
| cellulose microcrystalline PH 200 | 250 |
| talc | 7 |
| magnesium stearate | 5 |
| anhydrous colloidal silica | 3 |
| white Opadry ® | 8 |
| (= mixture of hydroxypropyl-methylcellulose, polyethyleneglycol 6000 and titatium dioxide) | |
| Excipients B | |
| cellulose microcrystalline PH 200 | 450 |
| talc | 7 |
| magnesium stearate | 5 |
| anhydrous colloidal silica | 3 |
| white Opadry ® | 8 |

The invention claimed is:

1. A method for treating obesity or overweight in non-diabetic mammals, which comprises orally administering to said obese or overweight non-diabetic mammal in need thereof an effective amount of a compound formed of tungsten (VI) and a pharmaceutically acceptable chemical moiety, or a solvate of said compound, in combination with pharmaceutically acceptable excipients, sufficient to therapeutically or cosmetically treat said obesity or overweight in said non-diabetic mammal.

2. The method of claim 1, wherein the compound of tungsten (VI) is a salt of tungstate comprising a pharmaceutically acceptable cationic moiety.

3. The method of claim 2, wherein the cationic moiety is selected from the group consisting of sodium, potassium, magnesium and calcium cations.

4. The method of claim 3, wherein the compound of tungsten (VI) is sodium tungstate ($Na_2WO_4$).

5. The method of claim 3, wherein the compound of tungsten (VI) is sodium tungstate and the solvate is sodium tungstate dihydrate.

* * * * *